United States Patent [19]

Kanemaru et al.

[11] Patent Number: 5,616,442
[45] Date of Patent: Apr. 1, 1997

[54] ELECTROPHOTOGRAPHIC PHOTOSENSITIVE MEMBER AND ELECTROPHOTOGRAPHIC APPARATUS USING SAME

[75] Inventors: Tetsuro Kanemaru, Tokyo; Toshihiro Kikuchi, Yokohama; Akihiro Senoo, Tokyo; Kouichi Nakata, Yokohama, all of Japan

[73] Assignee: Canon Kabushiki Kaisha, Tokyo, Japan

[21] Appl. No.: 631,610

[22] Filed: Apr. 10, 1996

Related U.S. Application Data

[63] Continuation of Ser. No. 266,520, Jun. 28, 1994, abandoned.

[30] Foreign Application Priority Data

Jun. 30, 1993 [JP] Japan ..................... 5-183185

[51] Int. Cl.$^6$ ..................................... G03G 5/06
[52] U.S. Cl. ................ 430/83; 430/96; 399/116; 399/161
[58] Field of Search ................ 430/59, 66, 67, 430/83, 96; 355/211

[56] References Cited

U.S. PATENT DOCUMENTS

| | | | |
|---|---|---|---|
| 4,931,371 | 6/1990 | Matsumoto et al. | 430/59 |
| 4,963,450 | 10/1990 | Miyazaki et al. | 430/59 |
| 5,024,912 | 6/1991 | Neishi et al. | 430/59 |
| 5,079,118 | 1/1992 | Kikuchi et al. | 430/59 |
| 5,202,207 | 4/1993 | Kanemaru et al. | 430/59 |
| 5,262,261 | 11/1993 | Kikuchi et al. | 430/59 |
| 5,356,742 | 10/1994 | Shimada et al. | 430/59 |
| 5,382,692 | 1/1995 | Shimada et al. | 430/59 |

FOREIGN PATENT DOCUMENTS

| | | |
|---|---|---|
| 318916 | 6/1989 | European Pat. Off. . |
| 376313 | 7/1990 | European Pat. Off. . |
| 52-4188 | 2/1977 | Japan . |
| 54-151955 | 11/1979 | Japan . |
| 55-42380 | 10/1980 | Japan . |
| 58-198043 | 11/1983 | Japan . |
| 1-100151 | 4/1989 | Japan . |
| 3-114058 | 6/1989 | Japan . |
| 55-52063 | 4/1990 | Japan . |
| 5-53349 | 3/1993 | Japan . |

*Primary Examiner*—John Goodrow
*Attorney, Agent, or Firm*—Fitzpatrick, Cella, Harper & Scinto

[57] ABSTRACT

An electrophotographic photosensitive member is constituted by disposing a photosensitive layer on a support. The photosensitive layer is characterized by containing a specific triphenylamine compound having at least two phenyl groups each substituted with two alkyl groups including one alkyl group located in meta-position in conjunction with nitrogen atom or each substituted with three alkyl groups. The photosensitive member is suitable for providing an electrophotographic apparatus showing excellent electrophotographic characteristics such as a high photosensitivity, a good potential stability in repetitive use, a decreased transfer memory, no crack in the photosensitive layer and no crystallization of a charge-transporting material.

18 Claims, 2 Drawing Sheets

ELECTROPHOTOGRAPHIC PHOTOSENSITIVE MEMBER AND ELECTROPHOTOGRAPHIC APPARATUS USING SAME

This application is a continuation of application Ser. No. 08/266,520 filed Jun. 28, 1994, now abandoned.

FIELD OF THE INVENTION AND RELATED ART

The present invention relates to an electrophotographic photosensitive member (hereinafter, sometimes referred to as "photosensitive member"), particularly to an electrophotographic photosensitive member having a photosensitive layer containing a specific triphenylamine compound.

The present invention also relates to an electrophotographic apparatus using the electrophotographic photosensitive member.

Heretofore, there have been proposed inorganic photosensitive members containing a photosensitive layer comprising an inorganic photoconductive material such as selenium, zinc oxide or cadmium as a main component. The inorganic photosensitive members, however, have encountered some problems such as poor film-forming properties, a low plasticity and an expensive production cost. The inorganic photoconductive material generally has a high toxicity. Accordingly, there have been large constraints on production of the photosensitive member and handling of the inorganic photoconductive material.

On the other hand, many organic photosensitive members containing organic photoconductive materials as a main component have remedied the above drawbacks of the inorganic photosensitive members and have attracted considerable attention, thus having been proposed and also having been put into practical use in some cases. As the organic photoconductive material for use in the organic photosensitive member, there have been proposed a charge transfer complex containing an organic photoconductive material such as poly-N-vinyl carbazole and Lewis acid such as 2,4,7-trinitro-9-fluorenone. These organic photoconductive material have been excellent in light weight properties and film-forming properties but are inferior to the inorganic photoconductive material with respect to sensitivity, durability, stability against environmental change, etc.

Accordingly, there has been proposed a photosensitive member having a laminate-type structure, wherein a photosensitive layer comprises a charge generation layer (CGL) containing a charge-generating substance (CGS) such as organic photoconductive dyes or pigments and a charge transport layer (CTL) containing a charge-transporting substance (CTS) (i.e., so-called "function-separation type photosensitive member"). Such a function-separation type photosensitive member has brought about a considerable improvement in a conventional photosensitive member having defects such as low sensitivity and poor durability.

The function-separation type photosensitive member allows a wide latitude in selecting a CGS and a CTS. As a result, it is possible to prepare readily a photosensitive member having an arbitrary characteristic.

As examples of the CGS, there are known various materials such as azo pigments, polycyclic quinone pigments, cyanine colorants, squaric acid dyes and pyrylium salt-type colorants. In the above CGS, many azo pigments have been proposed since the azo pigments have a good light-resistance, a large charge-generating ability, ease of synthesis, etc.

On the other hand, as examples of the CTS, there have been known various materials including: a pyrazoline compound as disclosed in Japanese Patent Publication (JP-B) No. 4188/1977; a hydrazone compound as disclosed in JP-B 42380/1980 or Japanese Laid-Open Patent Application (JP-A) No. 52063/1980; a triphenylamine compound as disclosed in JP-A 114058/1991 or JP-A 53349/1993; and a stilbene compound as disclosed in JP-A 151955/1979 or JP-A 198043/1983. The above triphenylamine compounds were different from those used in the present invention and did not necessarily show sufficient electrophotographic characteristics required to a practical CTS.

In an electrophotographic apparatus, a member such as a cleaning blade comes in contact with a photosensitive member. When the photosensitive member is not used for a long period of time in such a state, a crack in a charge transport layer or a phase separation due to a crystallization of a CTS is caused to occur, thus leading to image defects. Further, in case where a protective layer is formed on a photosensitive layer in order to improve durability, a CTL is adversely affected by the protective layer, thus causing a crack in the CTL or a phase separation due to a crystallization of the CTS.

In a reversal development system meeting a recent need for digitalization, a primary charging potential is different between the cases of effecting and not effecting transfer charging (i.e., occurrence of so-called "transfer memory") since a polarity of a primary charging and a polarity of a transfer charging are opposite to each other. As a result, an irregularity in an image density is readily liable to occur in the resultant image.

SUMMARY OF THE INVENTION

An object of the present invention is to provide an electrophotographic photosensitive member free from occurrence of cracks in a charge transport layer or from occurrence of crystallization even in case where the photosensitive member is not used for a long period of time or is provided with a protective layer.

Another object of the present invention is to provide an electrophotographic photosensitive member having a good photosensitivity, stable electrophotographic characteristics even in repetitive use, and a decreased transfer memory in a reversal development system.

A further object of the present invention is to provide an electrophotographic apparatus including the electrophotographic photosensitive member as described above.

According to the present invention, there is provided an electrophotographic photosensitive member, comprising: a support and a photosensitive layer disposed on the support, wherein the photosensitive layer contains a triphenylamine compound having at least two phenyl groups each substituted with two alkyl groups including at least one alkyl group located in meta-position in conjunction with nitrogen atom.

According to the present invention, there is also provided an electrophotographic photosensitive member, comprising: a support and a photosensitive layer disposed on the support, wherein the photosensitive layer contains a triphenylamine compound having at least two phenyl groups each substituted with three alkyl groups.

According to the present invention, there is further provided an electrophotographic apparatus including the above-mentioned electrophotographic photosensitive member, charging means for charging the electrophotographic photosensitive member, image-exposure means for exposing the electrophotographic photosensitive member to light to form an electrostatic latent image, and developing means for developing the electrostatic latent image formed on the electrophotographic photosensitive member with a toner.

These and other objects, features and advantages of the present invention will become more apparent upon a consideration of the following description of the preferred embodiments of the present invention taken in conjunction with the accompanying drawings.

DETAILED DESCRIPTION OF THE INVENTION

The electrophotographic photosensitive member according to the present invention is characterized by a photosensitive layer, formed on a support, comprising a specific triphenylamine compound containing at least two phenyl groups each substituted with two or three alkyl groups.

The triphenylamine compound may be used as a charge transport substance and is represented by the following structural formula (I):

wherein $Ar_1$, $Ar_2$ and $Ar_3$ independently denote a phenyl group, and at least two of $Ar_1$, $Ar_2$ and $Ar_3$ independently have two or three alkyl groups as substituents.

The two or three alkyl groups may preferably include at least one alkyl group located in meta-position in conjunction with nitrogen atom of the triphenylamine compound. Particularly, in the case of using a triphenylamine compound containing two alkyl groups connected with each phenyl group, sufficient performances cannot be obtained unless the two alkyl groups include one alkyl group located in the above-mentioned meta-position.

The two or three alkyl groups may more preferably include at least one alkyl group located in meta-position and one alkyl group located in para-position in conjunction with nitrogen atom, respectively.

The above-mentioned alkyl group may preferably have 1–4 carbon atoms, i.e., may preferably be methyl, ethyl, propyl or butyl.

Specific and non-exhaustive examples of the above-mentioned triphenylamine compound may include those represented by the following structural formulas (Example Compound Nos. 1–51).

(1)

(2)

(3)

(4)

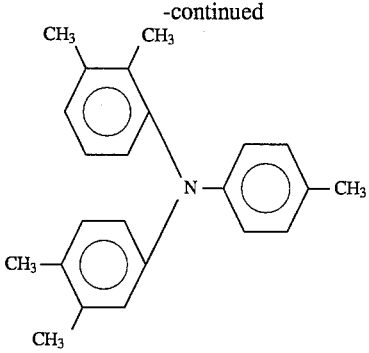
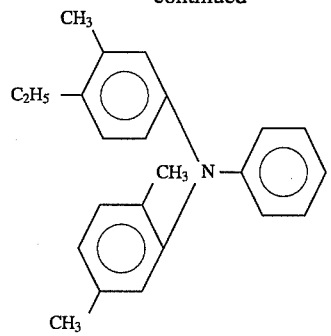

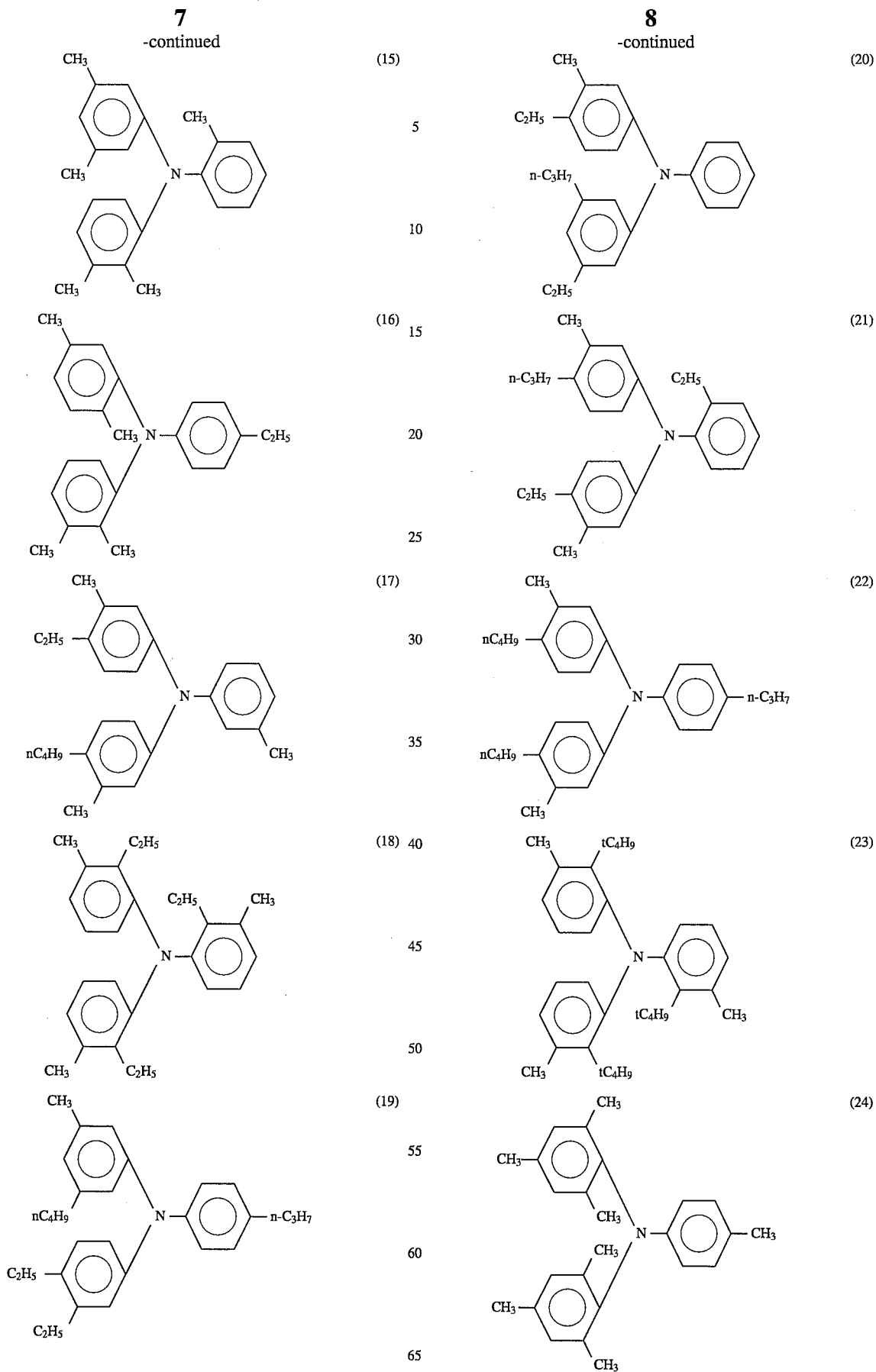

-continued
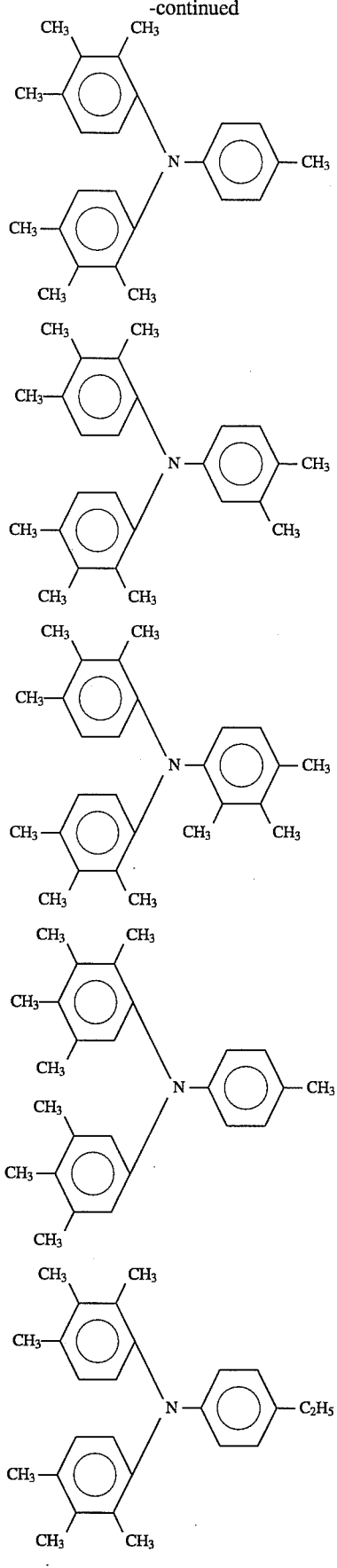
(25)
(26)
(27)
(28)
(29)
-continued
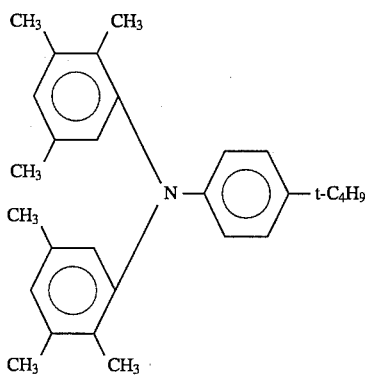
(30)
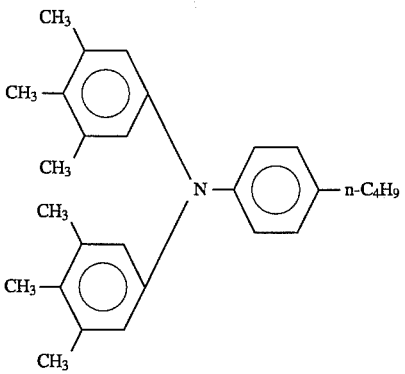
(31)
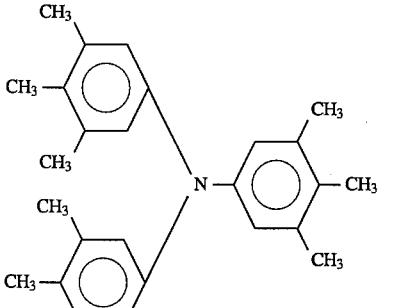
(32)
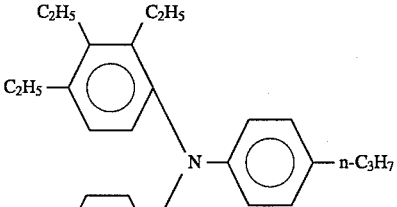
(33)

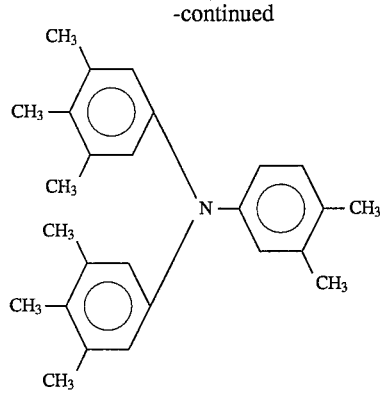
(34)
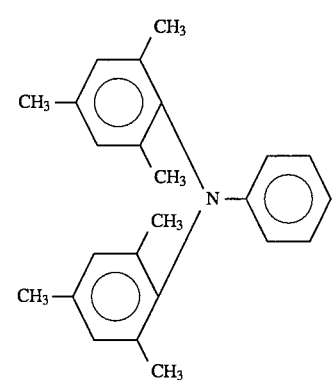
(35)
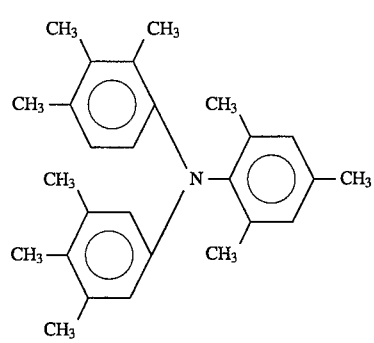
(36)
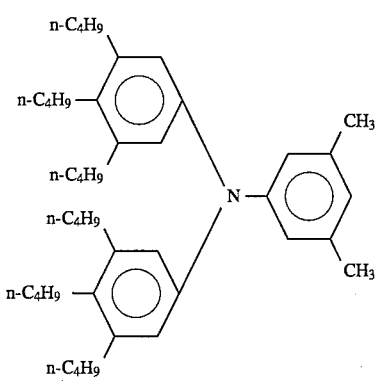
(37)
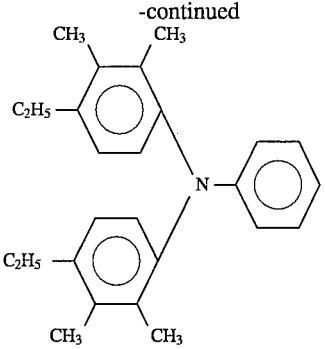
(38)
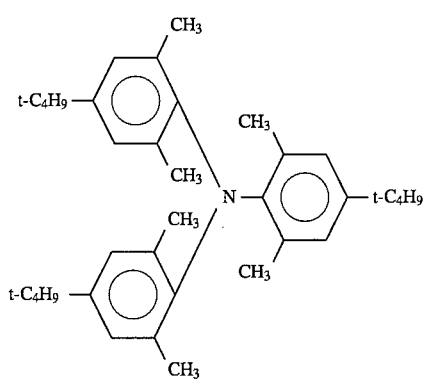
(39)
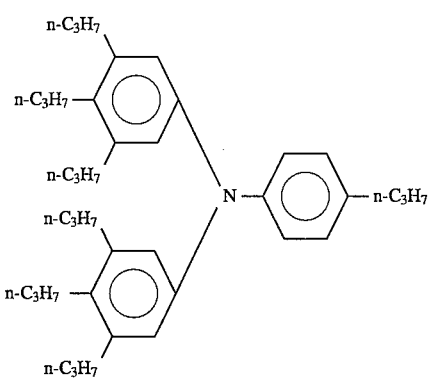
(40)
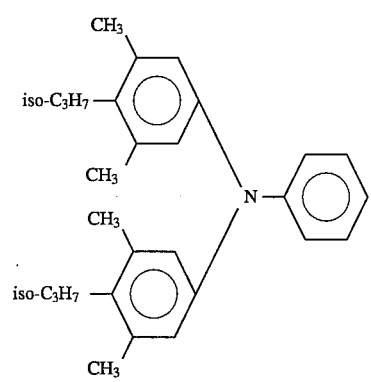
(41)

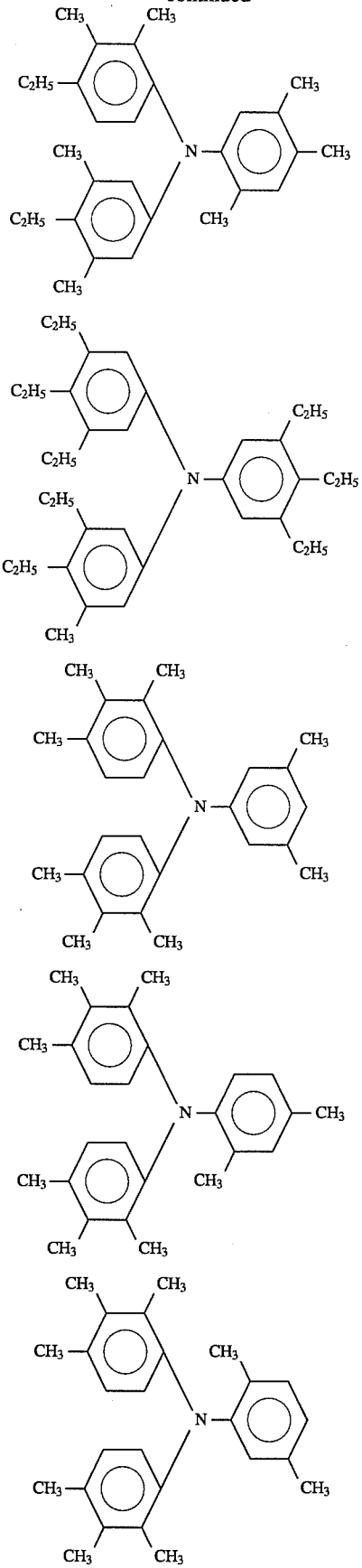
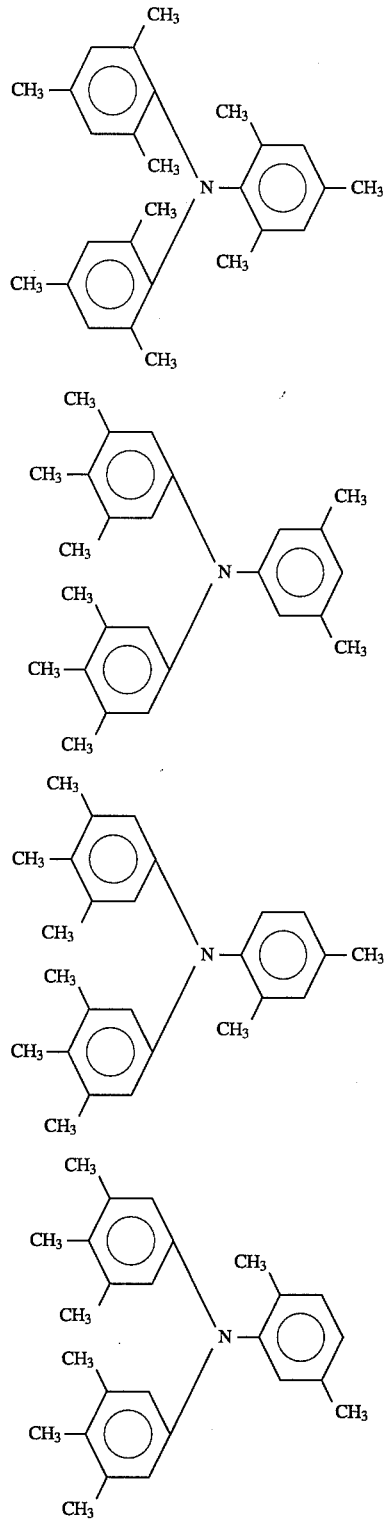

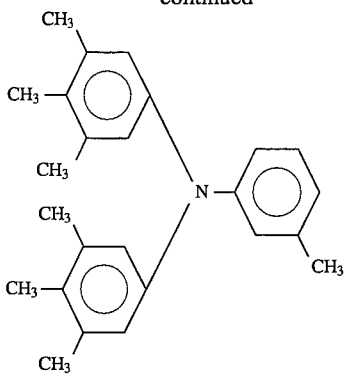

(51)

SYNTHESIS EXAMPLE 1

(Production of Ex. Comp. No. 11)

Figure 1:
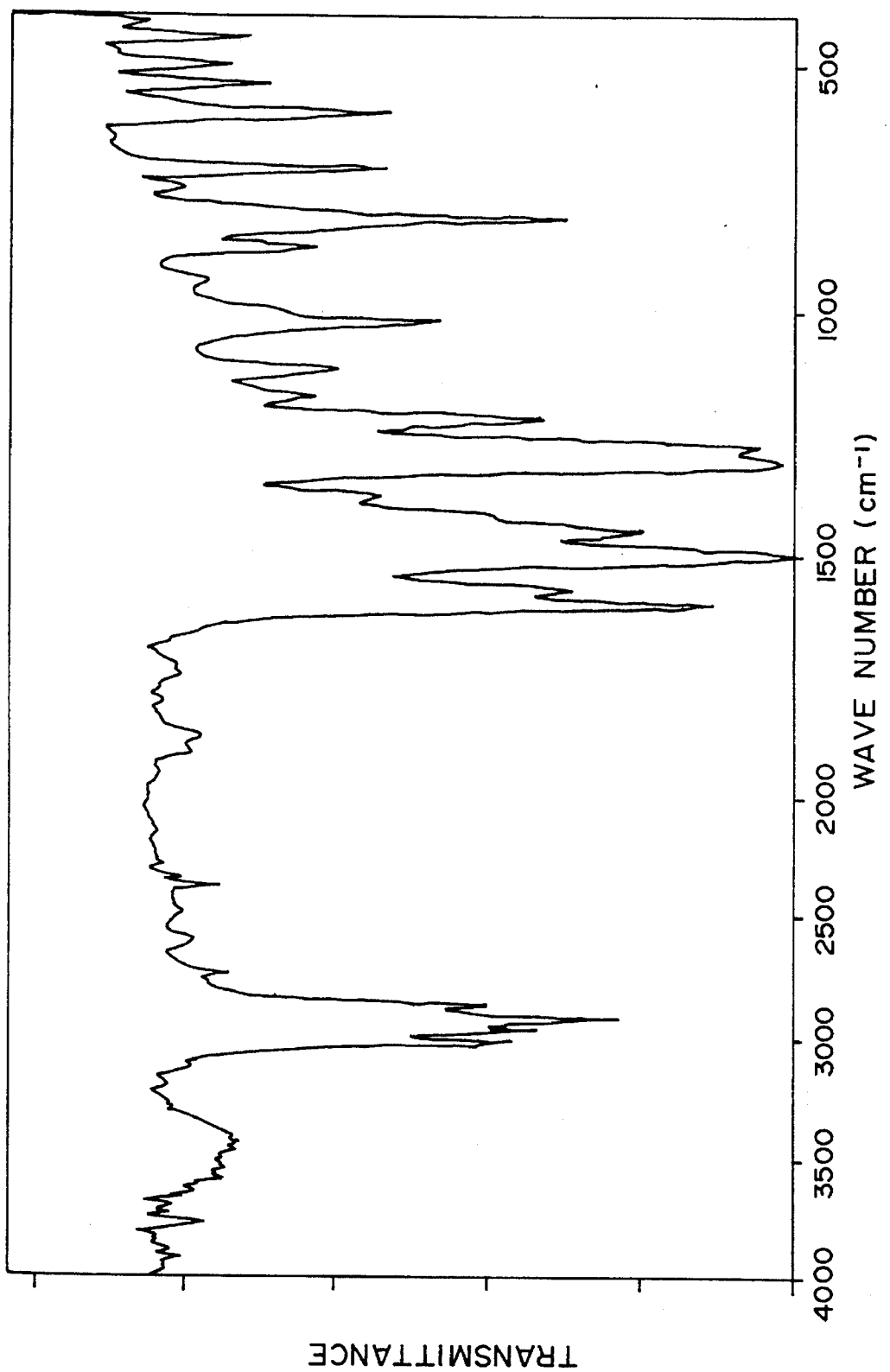
FIG. 1 is a graph showing an infrared absorption spectrum of a triphenylamine compound (Ex. Comp. No. 11) used in the present invention (according to KBr tablet method).

5.0 g (21.6 mM) of 3,4-dimethyliodobenzene, 0.96 g (9.0 mM) of toluidine, 27.6 g (200 mM) of potassium carbonate anhydride and 2.0 g of copper powder were added to 50 ml of o-dichlorobenzene, followed by heat-refluxing for 8 hours under stirring in nitrogen atmosphere. After cooling, the reaction mixture was subjected to filtration by means of suction, followed by distilling-off of o-dichlorobenzene from the filtrate under reduced pressure to obtain a residue. The residue was purified by silica gel column chromatography to obtain 22.4 g of an objective product (Ex. Comp. No. 11) (Yield: 79%). The product showed an infrared (IR) absorption spectrum, according to KBr tablet method, as shown in FIG. 1.

SYNTHESIS EXAMPLE 2

(Production of Ex. Comp. No. 25)

15.0 g (61.0 mM) of 2,3,4-trismethyliodobenzene, 2.6 g (24.4 mM) of toluidine, 18.0 g of potassium carbonate anhydride and 7.4 g of copper powder were added to 16 ml of o-dichlorobenzene, followed by heat-refluxing for 16 hours under stirring in nitrogen atmosphere. After cooling, the reaction mixture was subjected to filtration by means of suction, followed by distilling-off of o-dichlorobenzene from the filtrate under reduced pressure to obtain a residue. The residue was purified by silica gel column chromatography to obtain 5.27 g of an objective product (Ex. Comp. No. 25) (Yield: 62.9%).

Other triphenylamine compounds used in the present invention can be synthesized in the same manner as in Synthesis Examples 1 and 2.

The photosensitive member according to the present invention has a photosensitive layer containing a triphenylamine compound as described above, as a charge-transporting substance, and an appropriate charge-generating substance in combination.

The photosensitive layer of the electrophotographic photosensitive member of the present invention may, e.g., include the following layer structure:

(a) A laminated structure comprising a lower charge generation layer (CGL) containing a charge-generating substance (CGS) and an upper charge transport layer (CTL) containing a charge-transporting substance (CTS) successively formed on a support;

(b) A laminated structure comprising a lower CTL and an upper CGL successively formed on a support;

(c) A single layer containing a CGS and a CTS; and (d) A laminated structure comprising a lower CTL and an upper CTL containing a CGS and a CTS successively formed on a support.

The triphenylamine compound used in the present invention has a high hole-transporting ability and accordingly can be used as a charge-transporting substance (CTS). A polarity of a primary charge for use in a charging step of the photosensitive member of the present invention may preferably be negative for the structure (a), positive for the structure (b) and negative or positive for the structures (c) and (d).

The photosensitive member of the present invention may preferably contain a photosensitive layer having the above-mentioned layer structure (a). Hereinbelow, the photosensitive member containing such a photosensitive layer will be explained by way of preferred embodiment.

Examples of the CGS used in the invention may include:

(i) Azo pigments of monoazo-type, bisazo-type, trisazo-type, etc.;

(ii) Phthalocyanine pigments such as metallophthalocyanine and non-metallophthalocyanine;

(iii) Indigo pigments such as indigo and thioindigo;

(iv) Perylene pigments such as perylenic anhydride and perylenimide;

(v) Polycyclic quinones such as anthraquinone and pyrene-1,8-quinone;

(vi) Squarilium colorant;

(vii) Pyrilium salts and thiopyrilium salts;

(viii) Triphenylmethane-type colorants; and (ix) Inorganic substances such as selenium, selenium-tellurium and amorphous silicon.

The above CGS may be used singly or in combination of two or more species.

In the present invention, titanylphthalocyanine having the following formula:

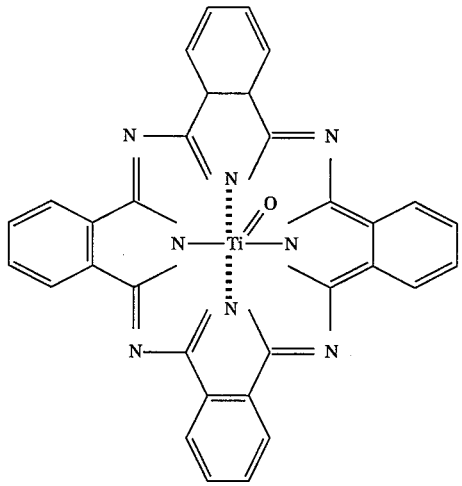

may preferably be used as a CGS.

As a CTS, it is possible to include a known CTS in the photosensitive layer in addition to the above-mentioned triphenylamine compound.

In the case of the photosensitive layer having the single layer structure (C), the photosensitive layer may preferably have a thickness of 5–100 μm, particularly 10–60 μm. The photosensitive layer may preferably contain a CGS and a CTS each in a proportion of 10–70 wt. %, particularly 20–70 wt. %.

In the case of the photosensitive layers having the laminated layer structures (a), (b) and (d), the CGL may preferably have a thickness of 0.001–5 μm, particularly 0.01–2 μm, and the CTL may preferably have a thickness of 5–40 μm, particularly 10–30 μm. The CGL may preferably contain a CGS in a proportion of 20–100 wt. %, particularly 50–100 wt. %. The CTL may preferably contain the triphenylamine compound used in the invention in an amount of 10–500 wt. parts per 100 wt. parts of a binder resin.

In the present invention, the photosensitive layer (of the single layer-type or the laminated layer-type) may be formed on a support by vapor-deposition, sputtering or chemical vapor deposition (CVD), or by dispersing materials used for the photosensitive layer in an appropriate solution containing a binder resin and applying the resultant coating liquid onto the support by means of a known coating method such as dipping, spray coating, spinner coating, roller coating, wire bar coating, or blade coating and then drying the coating. Examples of the binder resin used herein may be selected from various known resins such as polycarbonate resin, polyester resin, polyarylate resin, polyvinyl butyral resin, polystyrene resin, polyvinyl acetal resin, diallylphthalate resin, acrylic resin, methacrylic resin, vinyl acetate resin, phenolic resin, silicone resin, polysulfone resin, styrene-butadiene copolymer, alkyd resin, epoxy resin, urea resin and vinyl chloride-vinyl acetate copolymer. These binder resins may be used singly or in combination of two or more species.

Examples of the binder resin to be used for forming the CTL may include organic photoconductive polymers such as poly-N-vinylcarbazole and polyvinylanthracene in addition to the above resins.

The support constituting the photosensitive member of the present invention may be formed by using materials including: a metal or an alloy such as aluminum, aluminum alloy, copper, titanium or stainless steel; a polymeric material such as polyethylene terephthalate, phenolic resin, polypropylene or polystyrene; and rigid (or hard) paper. The shape of the support may preferably be in the form of a cylinder (or drum), belt or sheet. In case where the materials for the support have a higher volume resistivity, the materials are required to be subjected to an electroconductive treatment. Such an electroconductive treatment can be performed by forming an electroconductive film on the support or by dispersing an electroconductive substance within the support.

The photosensitive member according to the present invention may further include a protective layer on the photosensitive layer. The protective layer comprises a resinous material. Examples of such a resinous material may include: polyester, polyurethane, polyarylate, polyethylene, polystyrene, polybutadiene, polycarbonate, polyamide, polypropylene, polyimide, polyamideimide, polysulfone, polyaryl ether, polyacetal, nylon, phenolic resin, acrylic resin, silicone resin, epoxy resin, urea resin, allyl resin, alkyd resin, and butyral resin. The protective layer may preferably have a thickness of 0.05–15 μm, particularly 1–10 μm.

In the present invention, it is possible to dispose an undercoating layer between the support and the photosensitive layer for controlling charge injection properties at the interface therebetween or improving adhesive properties. The undercoating layer comprises a resinous material and further comprises an electroconductive material and a surfactant, as desired. Examples of such a resinous material may include: polyester, polyurethane, polyarylate, polyethylene, polystyrene, polybutadiene, polycarbonate, polyamide, polypropylene, polyimide, polyamideimide, polysulfone, polyaryl ether, polyacetal, nylon, phenolic resin, acrylic resin, silicone resin, epoxy resin, urea resin, allyl resin, alkyd resin, and butyral resin. The protective layer may preferably have a thickness of 0.05–7 μm, particularly 0.1–2 μm.

The photosensitive layer may further contain additives such as a sensitizer, antioxidant, ultraviolet absorbing agent and plasticizer, as desired.

Then, the electrophotographic apparatus using the photosensitive member according to the present invention will be explained.

Figure 2:
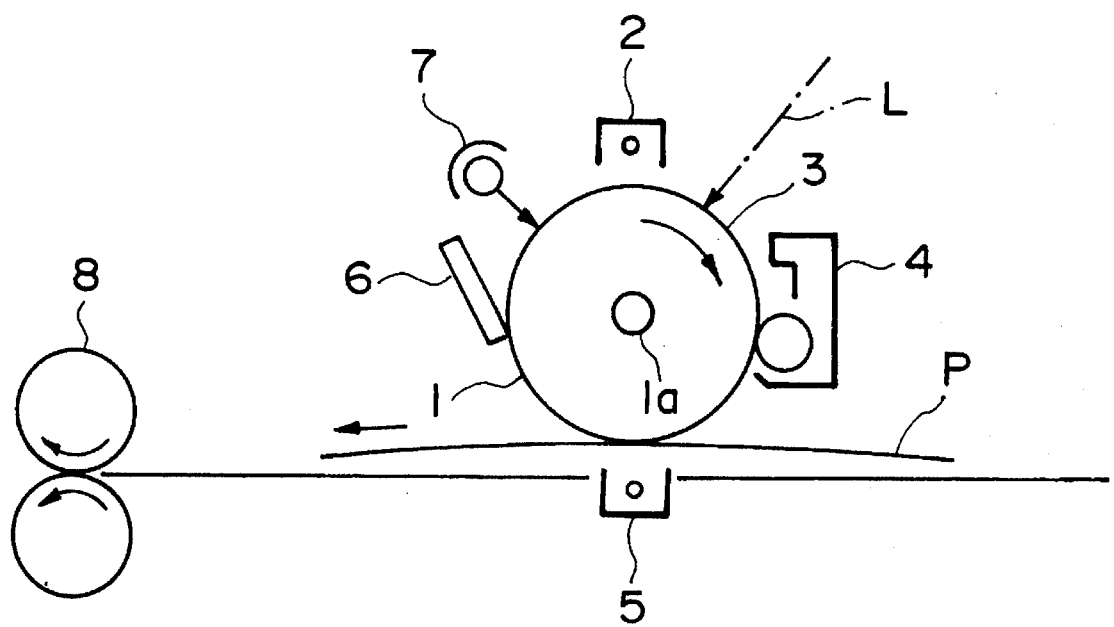
FIG. 2 is a schematic structural view of an embodiment of an electrophotographic apparatus using the electrophotographic photosensitive member according to the present invention.

FIG. 2 shows a schematic structural view of an electrophotographic apparatus using an electrophotographic photosensitive member of the invention. Referring to FIG. 2, a photosensitive drum (i.e., photosensitive member) 1 as an image-carrying member is rotated about an axis 1a at a prescribed peripheral speed in the direction of the arrow shown inside of the photosensitive drum 1. The surface of the photosensitive drum is uniformly charged by means of a charger (charging means) 2 to have a prescribed positive or negative potential. At an exposure part 3, the photosensitive drum 1 is exposed to light-image L (as by slit exposure or laser beam-scanning exposure) by using an image exposure means (not shown), whereby an electrostatic latent image corresponding to an exposure image is successively formed on the surface of the photosensitive drum 1. The electrostatic latent image is developed by a developing means 4 to form a toner image. The toner image is successively transferred to a recording material P which is supplied from a supply part (not shown) to a position between the photosensitive drum 1 and a transfer charger (transfer means) 5 in synchronism with the rotating speed of the photosensitive drum 1, by means of the transfer charger 5. The recording material P with the toner image thereon is separated from the photosensitive drum 1 to be conveyed to a fixing device 8, followed by image fixing to print out the recording material P as a copy outside the electrophotographic apparatus. Residual toner particles on the surface of the photosensitive drum 1 after the transfer are removed by means of a cleaner (cleaning means) 6 to provide a cleaned surface, and residual charge on the surface of the photosensitive drum 1 is erased by a pre-exposure means 7 to prepare for the next cycle. As the charger 2 for charging the photosensitive drum 1 uniformly, a corona charger is widely used in general. As the transfer charger 5, such a corona charger is also widely used in general.

According to the present invention, in the electrophotographic apparatus, it is possible to provide a device unit which includes plural means inclusive of or selected from the photosensitive member (photosensitive drum), the charger, the developing means, the cleaner, etc. so as to be attachable and detachable as desired. The device unit may, for example, be composed of the photosensitive member and at least one device of the charger, the developing means and the cleaner integrally supported to form a single unit capable of being attached to or detached from the body of the electrophotographic apparatus by using a guiding means such as a rail in the body.

In case where the electrophotographic apparatus is used as a copying machine or a printer, exposure light-image L may be given by reading a data on reflection light or transmitted light from an original or reading a data on the original, converting the data into a signal and then effecting a laser beam scanning, a drive of LED array or a drive of a liquid crystal shutter array so as to expose the photosensitive member to the light-image L.

The photosensitive member according to the present invention can be applied to not only an ordinary electrophotographic copying machine but also a facsimile machine, a laser beam printer, a light-emitting diode (LED) printer, a cathode-ray tube (CRT) printer, a liquid crystal printer, and other fields of applied electrophotography including, e.g., laser plate making.

Hereinbelow, the present invention, will be explained more specifically with reference to examples.

EXAMPLE 1

A coating liquid for a charge generation layer (CGL) was prepared by adding 3 g of a bisazo pigment of the formula:

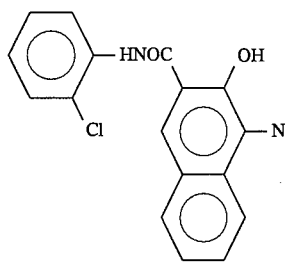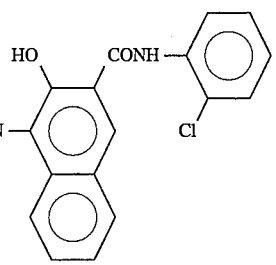

to a solution of 3 g of a butyral resin (butyral degree of 72 mol. %) in 80 ml of cyclohexanone and dispersing for 35 hours by means of a sand mill.

The coating liquid for the CGL was applied onto a 50 μm-thick aluminum sheet by a wire bar and dried to obtain a 0.21 μm-thick CGL.

Then, 10 g of a triphenylamine compound (Ex. Comp. No. 1) as a charge-transporting substance (CTS) and 9 g of a polycarbonate Z-type resin (weight-average molecular weight (Mw=35,000)) were dissolved in 65 g of monochlorobenzene to prepare a coating liquid.

The coating liquid was applied onto the above-prepared CGL by means of a wire bar, followed by drying to form a charge transport layer (CTL) having a thickness of 21 μm, whereby an electrophotographic photosensitive member according to the present invention was prepared.

The thus prepared photosensitive member was negatively charged by using corona (−5 KV) according to a static method by means of an electrostatic copying paper tester (Model: SP-428, mfd. by Kawaguchi Denki K.K.) and retained in a dark place for 1 sec. Thereafter, the photosensitive member was exposed to white light at an illuminance of 20 lux to evaluate charging characteristics. More specifically, the charging characteristics were evaluated by measuring a surface potential ($V_0$) at an initial stage (i.e., immediately after the charging), a surface potential ($V_1$) obtained after a dark decay for 1 sec, and the exposure quantity ($E_{1/5}$: lux.sec) (i.e., sensitivity) required for decreasing the potential $V_1$ to $\frac{1}{5}$ thereof.

In order to evaluate fluctuations of a light part potential ($V_L$) and a dark part potential ($V_D$), the above photosensitive member was attached to a cylinder for a photosensitive drum of a plain paper copying machine (PPC) NP-3825 (manufactured by Canon K.K.) and subjected to a copying test (or a durability test) of 3,000 sheets on condition that $V_D$ and $V_L$ at an initial stage were set to −700 V and −200 V, respectively.

The photosensitive member was also subjected to observation of a crack in a photosensitive layer and crystallization of a charge-transporting substance as follows.

Crack

The surface of a photosensitive member is touched or pressed by a finger to leave a fatty component of the finger to the surface of the photosensitive member, followed by standing for 8 hours under normal temperature and normal pressure. After a lapse of a prescribed hour, the touched part of the photosensitive member is observed to determine whether a crack is caused to occur or not.

Crystallization

The above-treated photosensitive member with a finger is left standing for one week at 75° C. in a constant temperature bath. After a lapse of a prescribed day, the touched part of the photosensitive member is observed to see whether an crystallization is caused to occur or not.

The above-mentioned evaluation results are shown in Table 1 appearing hereinafter.

EXAMPLES 2–8 and COMPARATIVE EXAMPLES 1–3

Electrophotographic photosensitive members were prepared and evaluated in the same manner as in Example 1 except for using the indicated compounds shown in Table 1 or shown below instead of the triphenylamine compound (Ex. Comp. No. 1), respectively.

In Comparative Examples 1–3, the following compounds were used, respectively.

Comp. Ex. 1

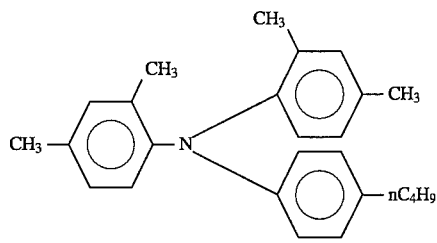

Comp. Ex. 2

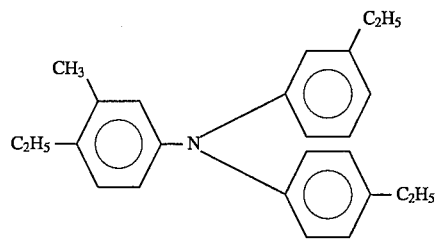

Comp. Ex. 3

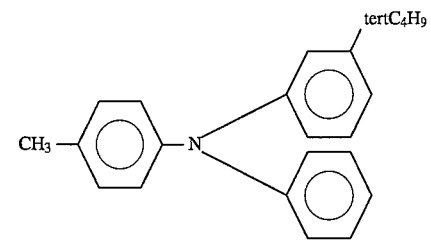

The results are also shown in Table 1.

TABLE 1

| Ex. No. | Comp. Ex. No. | Initial properties $V_0$ (−V) | $V_1$ (−V) | $E_{1/5}$ (lux.sec) | After 3,000 sheets $\Delta V_D$ (V) | $\Delta V_L$ (V) | Crack 1 hr | 2 hr | 4 hr | 8 hr | Crystallization 1 day | 3 day | 5 day | 7 day |
|---|---|---|---|---|---|---|---|---|---|---|---|---|---|---|
| Ex. 1 | No. 1 | 690 | 685 | 1.5 | −6 | +10 | o | o | o | o | o | o | o | o |
| 2 | 8 | 695 | 690 | 1.4 | −10 | +9 | o | o | o | o | o | o | o | o |
| 3 | 11 | 700 | 700 | 1.3 | −3 | +3 | o | o | o | o | o | o | o | o |
| 4 | 12 | 705 | 700 | 1.2 | −2 | ±0 | o | o | o | o | o | o | o | o |
| 5 | 16 | 705 | 700 | 1.5 | −7 | +8 | o | o | o | o | o | o | o | o |
| 6 | 18 | 690 | 690 | 1.6 | −8 | +7 | o | o | o | o | o | o | o | o |
| 7 | 22 | 700 | 695 | 1.3 | ±0 | +1 | o | o | o | o | o | o | o | o |
| 8 | 23 | 700 | 695 | 1.7 | −9 | +10 | o | o | o | o | o | o | o | o |
| Comp. Ex. 1 | — | 700 | 670 | 1.7 | −21 | +30 | o | o | o | x | o | o | o | o |
| 2 | — | 690 | 650 | 1.8 | −34 | +42 | o | o | x | x | o | o | o | x |
| 3 | — | 700 | 660 | 1.9 | −53 | +25 | o | x | x | x | o | x | x | x | o: No crack in a photosensitive layer or no crystallization of a CTS occurred.
x: A crack in a photosensitive layer or a crystallization of a CTS occurred.

EXAMPLE 9

Onto 50 μm-thick aluminum sheet, a solution of 4.7 g of an N-methoxymethylated 6-nylon resin (Mw=30,000) and 11 g of an alcohol-soluble copolymer nylon resin (Mw=30,000) in 90 g of methanol was applied by means of a wire bar, followed by drying to form a 1 μm-thick undercoating layer.

Then, 4.3 g of a charge-generating substance (CGS) represented by the formula shown below was added to a solution of 3.9 g of a phenoxy resin in 160 g of cyclohexanone and the resultant mixture was dispersed for 21 hours in a ball mill. The liquid dispersion was applied onto the undercoating layer by blade coating, followed by drying to form a 0.2 μm-thick CGL.

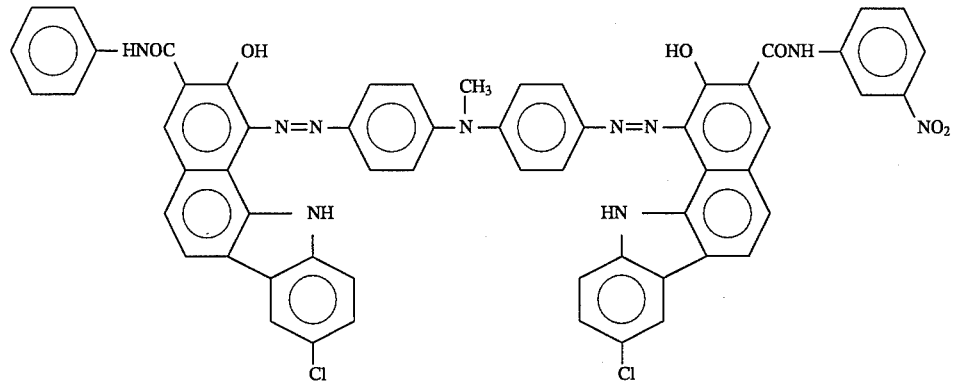

Then, 9 g of a triphenylamine compound (Ex. Comp. No. 4) and 10 g of a bisphenol Z-type resin (Mw=35,000) were dissolved in 69 g of monochlorobenzene. The solution was applied onto the CGL by blade coating and dried to form a 22 μm-thick CTL to prepare an electrophotographic photosensitive member.

The thus prepared photosensitive member was negatively charged by using corona (−5 KV) according to a static method by means of an electrostatic copying paper tester (Model: SP-428, mfd. by Kawaguchi Denki K.K.) and retained in a dark place for 1 sec. Thereafter, the photosensitive member was exposed to laser light to evaluate charging characteristics. More specifically, the charging characteristics were evaluated by measuring a surface potential ($V_0$) at an initial stage (i.e., immediately after the charging), a surface potential ($V_1$) obtained after a dark decay for 1 sec,
and the exposure quantity ($E_{1/6}$: μJ/cm$^2$) required for decreasing the potential $V_1$ to ⅙ thereof.

The light source used in this example was laser light (output: 5 mW, emission wavelength: 780 nm) emitted from a ternary semiconductor comprising gallium/aluminum/arsenic.

The above-mentioned photosensitive member was assembled in a laser beam printer (trade name: LBP-SX, mfd. by Canon K.K.) as an electrophotographic printer using a reversal development system, and subjected to measurement of a voltage ($V_{d1}$) of a primary charging under no transfer current application and a voltage ($V_{d2}$) of the primary charging under transfer current application to evaluate a transfer memory.($V_{d1}$-$V_{d2}$) and then subjected to image formation.

The image formation conditions used herein were as follows:

surface potential after primary charging: −700 V
surface potential after image exposure: −150 V (exposure quantity: 1.0 μJ/cm$^2$)
transfer potential: +700 V
polarity of developing: negative
process speed: 47 mm/sec
developing condition (developing bias): −450 V
image exposure scanning system: image scanning
exposure prior to the primary charging (pre-exposure: 8.0 lux.sec (whole surface exposure using red light)

The image formation was effected by line-scanning with laser beam in accordance with character and figure signals. As a result, good prints (images) were obtained with respect to the characters and figures.

Separately, the photosensitive member was evaluated in respect of a crack in the CTL and crystallization of the CTS in the same manner as in Example 1.

The results are shown in Table 2 appearing hereinafter.

EXAMPLES 10–14

Electrophotographic photosensitive members were prepared and evaluated in the same manner as in Example 9 except for using the indicated compounds shown in Table 2 instead of the triphenylamine compound (Ex. Comp. No. 4) used in Example 9, respectively.

The results are also shown in Table 2 appearing hereinafter.

COMPARATIVE EXAMPLES 4–6

Electrophotographic photosensitive members were prepared and evaluated in the same manner as in Example 9 except for using compounds shown below instead of the triphenylamine compound Ex. Comp. No. 4), respectively.

Comp. Ex. 4

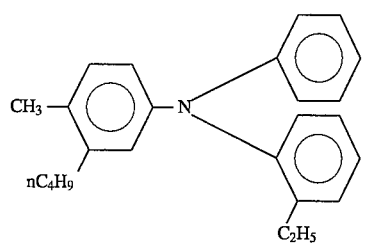

Comp. Ex. 5

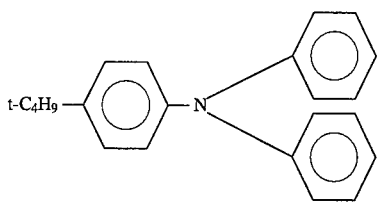

Comp. Ex. 6

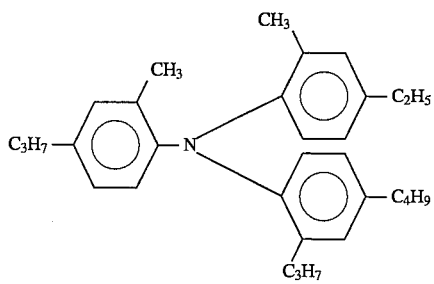

The results are also shown in Table 2 below.

TABLE 2

| Ex. No. | Ex. Comp. No. | Initial | | | Transfer memory | Crack | | | | Crystallization | | | |
|---|---|---|---|---|---|---|---|---|---|---|---|---|---|
| | | $V_D$ (−V) | $V_1$ (−V) | $E_{1/6}$(μJ/cm) | $V_{d1}$−$V_{d2}$ (V) | 1 hr | 2 hr | 4 hr | 8 hr | 1 day | 3 day | 5 day | 7 day |
| Ex. 9 | No. 4 | 700 | 690 | 1.6 | 15 | o | o | o | o | o | o | o | o |
| 10 | 6 | 705 | 700 | 1.5 | 13 | o | o | o | o | o | o | o | o |
| 11 | 11 | 705 | 700 | 1.3 | 10 | o | o | o | o | o | o | o | o |
| 12 | 12 | 700 | 690 | 1.3 | 12 | o | o | o | o | o | o | o | o |
| 13 | 16 | 700 | 700 | 1.6 | 15 | o | o | o | o | o | o | o | o |
| 14 | 21 | 705 | 700 | 1.5 | 15 | o | o | o | o | o | o | o | o |
| Comp. Ex. 4 | — | 705 | 670 | 1.8 | 40 | o | o | o | x | o | o | x | x |
| 5 | — | 700 | 660 | 1.9 | 55 | o | o | x | x | o | x | x | x |
| 6 | — | 700 | 680 | 2.2 | 70 | o | o | o | x | o | o | o | x | o: No crack in a photosensitive layer or no crystallization of a CTS occurred.
x: A crack in a photosensitive layer or a crystallization of a CTS occurred.

EXAMPLES 15–20

Electrophotographic photosensitive members were prepared and evaluated in the same manner as in Example 9 except for using a CGS shown below and the indicated compounds shown in Table 3, respectively.

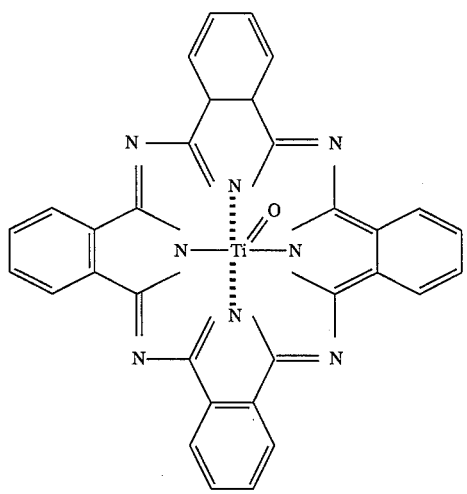

The results are shown in Table 3 below.

| | | | | Transfer | | | | | | | | |
|---|---|---|---|---|---|---|---|---|---|---|---|---|
| | Ex. Comp. | | Initial | | memory | Crack | | | | Crystallization | | | |
| Ex. No. | No. | $V_D$ (−V) | $V_1$ (−V) | $E_{1/6}$(μJ/cm) | $V_{d1}$−$V_{d2}$ (V) | 1 hr | 2 hr | 4 hr | 8 hr | 1 day | 3 day | 5 day | 7 day |
| Ex. 15 | No. 4 | 705 | 695 | 1.3 | 10 | o | o | o | o | o | o | o | o |
| 16 | 6 | 700 | 695 | 1.2 | 8 | o | o | o | o | o | o | o | o |
| 17 | 11 | 700 | 695 | 1.0 | 6 | o | o | o | o | o | o | o | o |
| 18 | 12 | 700 | 698 | 1.0 | 4 | o | o | o | o | o | o | o | o |
| 19 | 16 | 700 | 690 | 1.4 | 10 | o | o | o | o | o | o | o | o |
| 20 | 21 | 700 | 685 | 1.3 | 9 | o | o | o | o | o | o | o | o | o: No crack in a photosensitive layer or no crystallization of a CTS occurred.
x: A crack in a photosensitive layer or a crystallization of a CTS occurred.

EXAMPLE 21

A coating liquid was prepared by dispersing 4.4 g of 4-(4-dimethylaminophenyl)-2,6-diphenylthiapyrylium perchlorate and 5 g of a triphenylamine compound (Ex. Comp. No. 2) in a solution of 8 g of a polyester copolymer (Mw=46,000) in 100 g of a mixture solvent of a toluene/dioxane (1/1 by weight) for 20 hours by a ball mill. The coating liquid was applied onto a 50 μm-thick aluminum sheet by a wire bar and dried for 1 hour at 120° C. to form a 11 μm-thick photosensitive layer, whereby an electrophotographic photosensitive member was obtained.

The thus-prepared photosensitive member was evaluated in the same manner as in Example 1, whereby the following results were obtained.

| | |
|---|---|
| $V_0$: | −700 V |
| $V_1$: | −685 V |
| $E_{1/5}$: | 4.1 lux.sec |

No crack was generated even after 8 hours and no crystallization was observed even after one week.

EXAMPLE 22

A 30%-solution of an alcohol-soluble nylon resin (nylon 6-66-610-12 tetrapolymer) in methanol was applied onto a 50 μm-thick aluminum sheet and dried to form an undercoating layer having a thickness of 1.9 μm.

A solution of 9 g of a triphenylamine compound (Ex. Comp. No. 3) as a CTS and 10 g of a bisphenol A-type polycarbonate resin (Mw=28,000) in 75 g of a mixture solvent of monochlorobenzene/dichloromethane (3/1 by weight) was prepared and applied onto the above undercoating layer followed by drying to form a 20 μm-thick CTL.

Then, 4 g of a pigment of the formula:

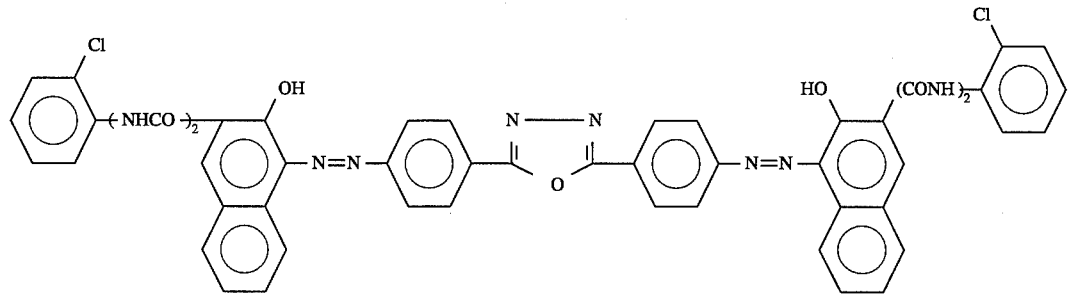

was added to a solution of 2.0 g of a butyral resin (butyral degree=63 mol %) in 65 ml of tetrahydrofuran, followed by stirring in a sand mill. The thus prepared coating liquid was applied onto the CTL by a wire bar and dried to form a 1.0 μm-thick CGL to prepare an electrophotographic photosensitive member.

The thus-prepared photosensitive member was evaluated in respect of charging characteristics in the same manner as in Example 1 except that the photosensitive member was positively charged. The results are shown below.

| | |
|---|---|
| $V_0$: | +710 V |
| $V_1$: | +701 V |
| $E_{1/5}$: | 2.4 lux.sec |

EXAMPLE 23

Onto a glass plate, a solution of 5 g of an N-methoxymethylated 6-nylon resin (Mw=28,000) and 9 g of an alcohol-soluble copolymer nylon resin (Mw=28,000) in a mixture solvent of 35 g of methanol and 65 g of butanol was applied by dipping, followed by drying to form a 1 micron-thick undercoating layer.

Subsequently, 10 g of a triphenylamine compound (Ex. Comp. No. 5) and 12 g of a bisphenol A-type polycarbonate resin (Mw=27,000) were dissolved in 100 g of a mixture solvent of monochlorobenzene/dichloromethane (4/6 by weight). The solution was applied onto the undercoating layer by wire bar coating and dried to form a CTL having a thickness of 17 μm.

Then, 60 g of an acrylate-type monomer of the formula:

$$HOCH_2-C+CH_2O-\underset{\underset{O}{\|}}{C}-CH_2CH_2CH_2CH_2O-C-\underset{H}{\overset{\|}{C}}=CH_2]_3,$$

40 g of tin oxide fine particles having an average particle size of 400 Å (before dispersion), 3 g of 2-methylthioxanthone and 280 g of methyl cellosolve were mixed and stirred for 72 hours in a sand mill. The resultant mixture was applied onto the CTL by beam coating and dried and then was cured by photopolymerization for 30 seconds with a high-pressure mercury lamp (light intensity of 8 mW/cm²) to form a 2.1 μm-thick protective layer, whereby a testing structure for evaluation of a crack and crystallization was prepared.

The testing structure was subjected to observation of occurrence of a crack and crystallization with a transmission microscope (magnification: 10) as follows.

From the back side (the glass plate side) of the testing structure, light was emitted to the testing structure so as to form an incident angle (i.e., an angle formed by light arriving at the surface of the glass plate and the perpendicular to that surface at the point of arrival) of 75 degrees. As a result, no crack and crystallization were observed.

The testing structure used in this example was not a photosensitive member. However, the testing structure was usable for evaluation of effects by the protective layer formed on the CTL.

EXAMPLE 24

A coating liquid for a charge generation layer (CGL) was prepared by adding 3.2 g of a bisazo pigment of the formula:

to a solution of 3 g of a butyral resin (butyral degree of 72 mol. %) in 80 ml of cyclohexanone and dispersing for 24 hours by means of a sand mill.

The coating liquid for the CGL was applied onto a 50 μm-thick aluminum sheet by a wire bar and dried to obtain a 0.21 μm-thick CGL.

Then, 10 g of a triphenylamine compound (Ex. Comp. No. 24) as a charge-transporting substance (CTS) and 10 g of a polycarbonate Z-type resin (weight-average molecular weight (Mw=20,000)) were dissolved in 68 g of monochlorobenzene to prepare a coating liquid.

The coating liquid was applied onto the above-prepared CGL by means of a wire bar, followed by drying to form a charge transport layer (CTL) having a thickness of 25 μm, whereby an electrophotographic photosensitive member according to the present invention was prepared.

The thus prepared photosensitive member was evaluated in the same manner as in Example 1.

The results are shown in Table 4 appearing hereinafter.

EXAMPLES 25–32 and COMPARATIVE EXAMPLE 7

Electrophotographic photosensitive members were prepared and evaluated in the same manner as in Example 24 except for using the indicated compounds shown in Table 4 or shown below instead of the triphenylamine compound (Ex. Comp. No. 24 used in Example 24), respectively.

In Comparative Example 7, the following compound was used.

Comp. Ex. 7

The results are also shown in Table 4 below.

TABLE 4

| Ex. No. | Ex. Comp. No. | Initial properties | | | After 3,000 sheets | | Crack | | | | Crystallization | | | |
|---|---|---|---|---|---|---|---|---|---|---|---|---|---|---|
| | | $V_0$ (−V) | $V_1$ (−V) | $E_{1/5}$ (lux.sec) | $\Delta V_D$ (V) | $\Delta V_L$ (V) | 1 hr | 2 hr | 4 hr | 8 hr | 1 day | 3 day | 5 day | 7 day |
| Ex. 24 | No. 24 | 705 | 701 | 1.7 | −7 | +10 | o | o | o | o | o | o | o | o |
| 25 | 27 | 710 | 703 | 1.7 | −7 | +9 | o | o | o | o | o | o | o | o |
| 26 | 30 | 700 | 687 | 1.6 | −6 | +8 | o | o | o | o | o | o | o | o |
| 27 | 31 | 702 | 694 | 1.5 | −5 | +5 | o | o | o | o | o | o | o | o |
| 28 | 32 | 699 | 690 | 1.4 | −4 | +5 | o | o | o | o | o | o | o | o |
| 29 | 34 | 692 | 687 | 1.4 | −3 | +5 | o | o | o | o | o | o | o | o |
| 30 | 45 | 705 | 696 | 1.7 | −10 | +7 | o | o | o | o | o | o | o | o |
| 31 | 47 | 707 | 700 | 1.8 | −10 | +12 | o | o | o | o | o | o | o | o |
| 32 | 51 | 700 | 695 | 1.5 | −8 | +7 | o | o | o | o | o | o | o | o |
| Comp. Ex. 7 | — | 690 | 650 | 1.9 | −19 | +24 | o | o | x | x | o | o | o | x | o: No crack in a photosensitive layer or no crystallization of a CTS occurred.
x: A crack in a photosensitive layer or a crystallization of a CTS occurred.

EXAMPLE 33

Onto 50 μm-thick aluminum sheet, a solution of 6.0 g of an N-methoxymethylated 6-nylon resin (Mw=30,000) and 10.0 g of an alcohol-soluble copolymer nylon resin (Mw=30,000) in 92 g of methanol was applied by means of a wire bar, followed by drying to form a 1 μm-thick undercoating layer.

Then, 3.2 g of a charge-generating substance (CGS) represented by the formula shown below was added to a solution of 3.0 g of a phenoxy resin in 160 g of cyclohexanone and the resultant mixture was dispersed for 24 hours in a ball mill. The liquid dispersion was applied onto the undercoating layer by blade coating, followed by drying to form a 0.2 μm-thick CGL.

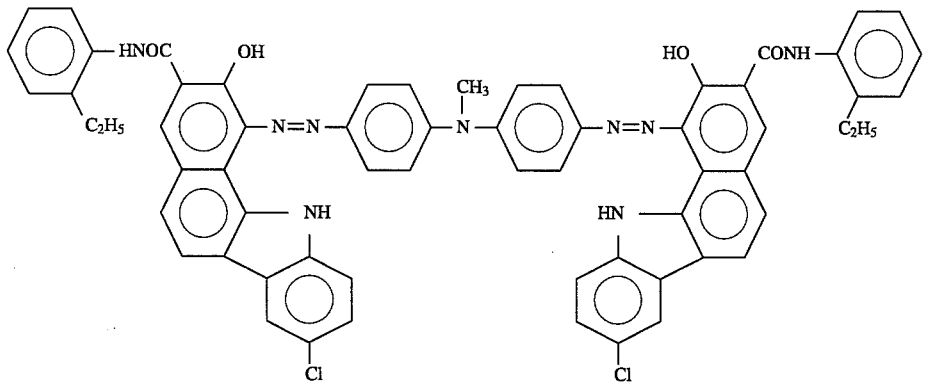

Then, 9.5 g of a triphenylamine compound (Ex. Comp. No. 27) and 10 g of a bisphenol Z-type resin (Mw=40,000) were dissolved in 68 g of monochlorobenzene. The solution was applied onto the CGL by blade coating and dried to form a 25 μm-thick CTL to prepare an electrophotographic photosensitive member.

The thus prepared photosensitive members were evaluated in the same manner as in Example 9 in respects of charging characteristics, a crack in the CTL and a crystallization of the CTS. The results are shown in Table 5.

Further, when each of the photosensitive members was subjected to image formation by means of a laser beam printer in the same manner as in Example 9, good prints (images) of characters and figures were obtained.

EXAMPLES 34–38

Electrophotographic photosensitive members were prepared and evaluated in the same manner as in Example 33 except for using the indicated compounds shown in Table 5 instead of the triphenylamine compound (Ex. Comp. No. 27) used in Example 33, respectively.

The results are also shown in Table 5 appearing hereinafter.

COMPARATIVE EXAMPLE 8

An electrophotographic photosensitive member was prepared and evaluated in the same manner as in Example 33 except for using a compound shown below instead of the triphenylamine compound Ex. Comp. No. used in Example 33).

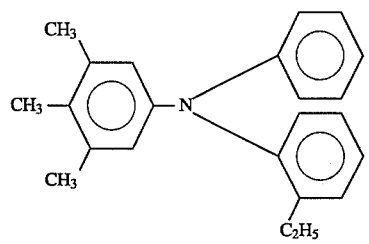

The results are also shown in Table 5 below.

TABLE 5

| Ex. No. | Ex. Comp. No. | Initial $V_D$ (−V) | $V_1$ (−V) | $E_{1/6}$(μJ/cm) | Transfer memory $V_{d1}$−$V_{d2}$ (V) | Crack 1 hr | 2 hr | 4 hr | 8 hr | Crystallization 1 day | 3 day | 5 day | 7 day |
|---|---|---|---|---|---|---|---|---|---|---|---|---|---|
| Ex. 33 | No. 27 | 705 | 692 | 1.8 | 17 | o | o | o | o | o | o | o | o |
| 34 | 28 | 706 | 701 | 1.6 | 14 | o | o | o | o | o | o | o | o |
| 35 | 32 | 700 | 693 | 1.5 | 14 | o | o | o | o | o | o | o | o |
| 36 | 37 | 699 | 690 | 1.6 | 15 | o | o | o | o | o | o | o | o |
| 37 | 40 | 696 | 698 | 1.6 | 16 | o | o | o | o | o | o | o | o |
| 38 | 46 | 708 | 700 | 1.8 | 17 | o | o | o | o | o | o | o | o |
| Comp. Ex. 8 | — | 701 | 690 | 2.2 | 40 | o | o | x | x | o | o | o | x | o: No crack in a photosensitive layer or no crystallization of a CTS occurred.
x: A crack in a photosensitive layer or a crystallization of a CTS occurred.

EXAMPLES 39–44

Electrophotographic photosensitive members were prepared and evaluated in the same manner as in Example 33 except for using a CGS shown below and the indicated compounds shown in Table 6, respectively.

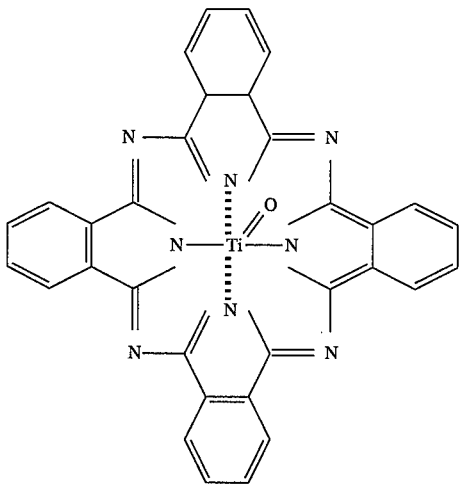

The results are shown in Table 6 below.

(Mw=40,000) in 80 g of a mixture solvent of a toluene/dioxane (1/1 by weight) for 24 hours by a ball mill. The coating liquid was applied onto a 50 μm-thick aluminum sheet by a wire bar and dried for 1 hour at 120° C. to form a 10 μm-thick photosensitive layer, whereby an electrophotographic photosensitive member was obtained.

The thus-prepared photosensitive member was evaluated in the same manner as in Example 1, whereby the following results were obtained.

| | |
|---|---|
| $V_0$: | −695 V |
| $V_1$: | −683 V |
| $E_{1/5}$: | 4.4 lux.sec |

No crack was generated even after 8 hours and no crystallization was observed even after one week.

EXAMPLE 46

A 30%-solution of an alcohol-soluble nylon resin (nylon 6-66-610-12 tetrapolymer) in methanol was applied onto a 50 μm-thick aluminum sheet and dried to form an undercoating layer having a thickness of 1.2 μm.

A solution of 9.5 g of a triphenylamine compound (Ex. Comp. No. 36) as a CTS and 10 g of a bisphenol A-type polycarbonate resin (Mw=20,000) in 75 g of a mixture

TABLE 6

| Ex. No. | Ex. Comp. No. | Initial $V_D$ (−V) | $V_1$ (−V) | $E_{1/6}$(μJ/cm) | Transfer memory $V_{d1}$−$V_{d2}$ (V) | Crack 1 hr | 2 hr | 4 hr | 8 hr | Crystallization 1 day | 3 day | 5 day | 7 day |
|---|---|---|---|---|---|---|---|---|---|---|---|---|---|
| Ex. 39 | No. 27 | 704 | 692 | 1.5 | 11 | o | o | o | o | o | o | o | o |
| 40 | 28 | 703 | 700 | 1.4 | 10 | o | o | o | o | o | o | o | o |
| 41 | 32 | 705 | 702 | 1.2 | 8 | o | o | o | o | o | o | o | o |
| 42 | 37 | 698 | 695 | 1.3 | 9 | o | o | o | o | o | o | o | o |
| 43 | 40 | 702 | 698 | 1.5 | 11 | o | o | o | o | o | o | o | o |
| 44 | 46 | 704 | 700 | 1.6 | 11 | o | o | o | o | o | o | o | o | o: No crack in a photosensitive layer or no crystallization of a CTS occurred.
x: A crack in a photosensitive layer or a crystallization of a CTS occurred.

EXAMPLE 45

A coating liquid was prepared by dispersing 4.4 g of 4-(4-dimethylaminophenyl)-2,6-diphenylthiapyrylium perchlorate and 5 g of a triphenylamine compound (Ex. Comp. No. 2) in a solution of 8 g of a polyester copolymer solvent of monochlorobenzene/dichloromethane (3/1 by weight) was prepared and applied onto the above undercoating layer followed by drying to form a 18 μm-thick CTL.

Then, 3.2 g of a pigment of the formula:

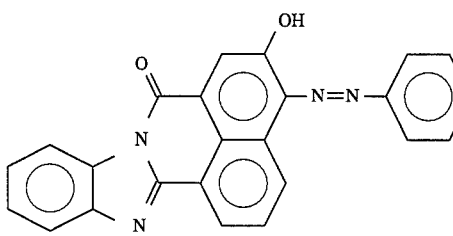 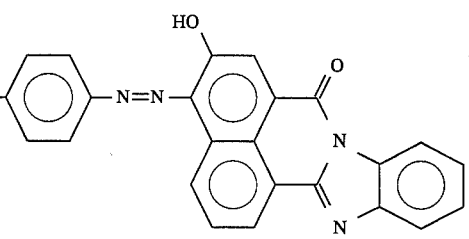

was added to a solution of 2.0 g of a butyral resin (butyral degree=63 mol %) in 70 ml of tetrahydrofuran, followed by stirring in a sand mill. The thus prepared coating liquid was applied onto the CTL by a wire bar and dried to form a 0.8 µm-thick CGL to prepare an electrophotographic photosensitive member.

The thus-prepared photosensitive member was evaluated in respect of charging characteristics in the same manner as in Example 1 except that the photosensitive member was positively charged. The results are shown below.

| | |
|---|---|
| $V_0$: | +700 V |
| $V_1$: | +692 V |
| $E_{1/5}$: | 3.1 lux.sec |

EXAMPLE 47

A testing structure was prepared in the same manner as in Example 23 except that a CTL was formed as follows.

10 g of a triphenylamine compound (Ex. Comp. No. 39) and 12 g of a bisphenol A-type polycarbonate resin (Mw=20,000) were dissolved in 100 g of a mixture solvent of monochlorobenzene/dichloromethane (4/6 by weight). The solution was applied onto the undercoating layer by wire bar coating and dried to form a CTL having a thickness of 20 µm.

When the thus prepared testing structure was subjected to observation through a transmission microscope in the same manner as in Example 23, no crack and crystallization were caused to occur.

As described above, according to the present invention, there is provided an electrophotographic photosensitive member causing no crack in a CTL (or photosensitive layer) and no phase separation due to a crystallization of a CTS and having a good photosensitivity and stable electrophotographic characteristics even in repetitive use. The photosensitive member little cause transfer memory in a reversal development system. Thus, the photosensitive member provides good images free from defects and retains a stable image quality even in repetitive image formation.

What is claimed is:

1. An electrophotographic photosensitive member, comprising: a support and a photosensitive layer disposed on the support,
   wherein said photosensitive layer contains a triphenylamine compound having at least two phenyl groups each substituted with two alkyl groups including at least one alkyl group located in meta-position in conjunction with nitrogen atom.

2. An electrophotographic photosensitive member, comprising: a support and a photosensitive layer disposed on the support,
   wherein said photosensitive layer contains a triphenylamine compound having at least two phenyl groups each substituted with three alkyl groups.

3. A member according to claim 2, wherein said three alkyl groups contain at least one alkyl group located in meta-position in conjunction with nitrogen atom.

4. A member according to claim 1 or 3, wherein said alkyl groups contain one alkyl group located in para-position in conjunction with nitrogen atom.

5. A member according to claim 1 or 2, wherein each of said alkyl groups has 1–4 carbon atoms.

6. A member according to claim 1 or 2, wherein said photosensitive layer contains a charge-generating substance comprising titanyl phthalocyanine represented by the following formula:

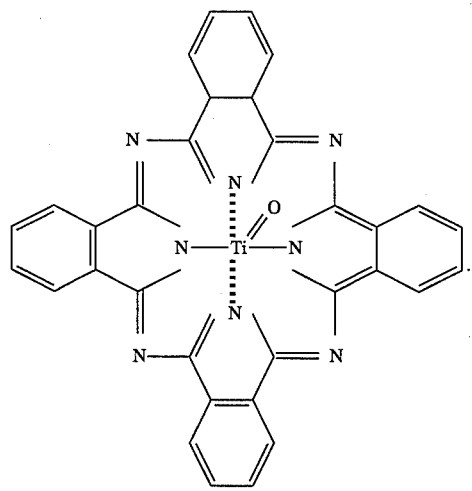

7. An electrophotographic apparatus, comprising: an electrophotographic photosensitive member according to claim 1, charging means for charging said electrophotographic photosensitive member, image-exposure means for exposing said electrophotographic photosensitive member to light to form an electrostatic latent image, and developing means for developing the electrostatic latent image formed on said electrophotographic photosensitive member with a toner.

8. A device unit, including: an electrophotographic photosensitive member according to claim 1 or 2 and at least one means selected from a charging means, a developing means, and a cleaning means;
   wherein said photosensitive member, and said at least one means selected from the charging means, the developing means, and the cleaning means are integrally supported to form a single unit, which can be removably attached to an apparatus body.

9. A member according to claim 1, wherein said photosensitive layer contains an azo pigment.

10. A member according to claim 1, further comprising a protective layer on said photosensitive layer.

11. An apparatus according to claim 7, wherein said photosensitive layer contains an azo pigment.

12. An apparatus according to claim 7, wherein said electrophotographic photosensitive member comprises a protective layer on said photosensitive layer.

13. An apparatus according to claim 7, wherein said developing means is a reversal developing means.

14. A unit according to claim 8, wherein said photosensitive layer contains an azo pigment.

15. A unit according to claim 8, wherein said electrophotographic photosensitive member comprises a protective layer on said photosensitive layer.

16. A unit according to claim 8, wherein said developing means is a reversal developing means.

17. An electrophotographic apparatus, comprising:
an electrophotographic photosensitive member according to claim 2, charging means for charging said electrophotographic photosensitive member, exposure means for exposing said electrophotographic photosensitive member to light to form an electrostatic latent image and developing means for developing the electrostatic latent image formed on said electrophotographic photosensitive member with a toner.

18. A device unit, including:
an electrophotographic photosensitive member according to claim 2 and at least one means selected from a charging means, a developing means and a cleaning means;
wherein said photosensitive member and said at least one means selected from the charging means, the developing means and the cleaning means are integrally supported to form a single unit, which can be removably attached to an apparatus body.

* * * * *

UNITED STATES PATENT AND TRADEMARK OFFICE
CERTIFICATE OF CORRECTION

PATENT NO. : 5,616,442

DATED : April 1, 1997

INVENTOR(S): TETSURO KANEMARU ET AL.

It is certified that error appears in the above-identified patent and that said Letters Patent is hereby corrected as shown below:

On title page,
   item [56] <u>REFERENCES CITED, FOREIGN PATENT DOCUMENTS</u>

"3-114058 6/1989 Japan" should read --3-114058 5/1991 Japan--.

"55-52063 4/1990 Japan" should read --55-52063 4/1980 Japan--.

<u>COLUMN 21, LINE 36</u>

" 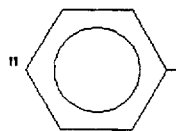-HNOC " should read -- 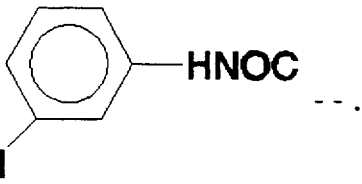 --.

<u>COLUMN 30</u>

Line 34, "Ex. Comp. No." should read --(Ex. Comp. No. 27)--.

Line 54, "33)." should read --33.--.

UNITED STATES PATENT AND TRADEMARK OFFICE
CERTIFICATE OF CORRECTION

PATENT NO. : 5,616,442

DATED : April 1, 1997

INVENTOR(S) : TETSURO KANEMARU ET AL.

It is certified that error appears in the above-identified patent and that said Letters Patent is hereby corrected as shown below:

COLUMN 34

Line 51, "claim 1 or 2," should read --claim 1,--.

COLUMN 36

Line 6, "claim 2" should read --claim 2,--.

Signed and Sealed this

Seventh Day of October, 1997

Attest:

Attesting Officer

BRUCE LEHMAN

Commissioner of Patents and Trademarks